United States Patent
Kawachi

(10) Patent No.: US 7,884,221 B2
(45) Date of Patent: Feb. 8, 2011

(54) METHOD OF SEPARATING ERGOSTEROL

(75) Inventor: Hideo Kawachi, Hyogo (JP)

(73) Assignee: Kaneka Corporation, Osaka-Shi (JP)

( * ) Notice: Subject to any disclaimer, the term of this patent is extended or adjusted under 35 U.S.C. 154(b) by 955 days.

(21) Appl. No.: 10/532,682

(22) PCT Filed: Nov. 7, 2003

(86) PCT No.: PCT/JP03/14170

§ 371 (c)(1),
(2), (4) Date: Apr. 26, 2005

(87) PCT Pub. No.: WO2004/046163

PCT Pub. Date: Jun. 3, 2004

(65) Prior Publication Data

US 2006/0167290 A1    Jul. 27, 2006

(30) Foreign Application Priority Data

Nov. 8, 2002  (JP) .............................. 2002-325381

(51) Int. Cl.
C07J 9/00 (2006.01)
A61K 31/56 (2006.01)

(52) U.S. Cl. ...................... 552/545; 552/540; 552/547

(58) Field of Classification Search ................ 552/544, 552/545, 547; 435/52
See application file for complete search history.

(56) References Cited

U.S. PATENT DOCUMENTS 1,775,548 A * 9/1930 Bills .......................... 552/547
1,842,929 A * 1/1932 Bills .......................... 552/545
2,536,753 A * 1/1951 Knol .......................... 552/545
4,447,362 A * 5/1984 Watanabe et al. ............ 552/307
5,498,138 A * 3/1996 Nimberger et al. ............ 417/46

FOREIGN PATENT DOCUMENTS

| | | |
|---|---|---|
| EP | 0 626 388 A2 | 11/1994 |
| EP | 0 626 388 A3 | 11/1994 |
| GB | 2 107 715 A | 5/1983 |
| JP | 50-142787 A | 11/1975 |
| JP | 2002-80492 A | 3/2002 |
| JP | 2002-80493 A | 3/2002 |
| JP | 2002-105097 A | 4/2002 |

OTHER PUBLICATIONS

Chemical Abstract, vol. 85, Abs. No. 134919, 2 pages, date: 1976.
International Search Report from Corresponding International Application No. PCT/JP03/14170, dated Mar. 9, 2004, 2 pages.

* cited by examiner

Primary Examiner—Frederick Krass
Assistant Examiner—Walter E Webb
(74) Attorney, Agent, or Firm—Kratz, Quintos & Hanson, LLP

(57) ABSTRACT

The present invention provides a method of separating ergosterol from a solution containing ergosterol in water-insoluble organic solvent, comprising supplying water to the solution and precipitating ergosterol. According to the method of the present invention, ergosterol crystals can be obtained at a high yield. Moreover, controlled water supply provides granular ergosterol aggregates exhibiting good solid-liquid separation character at a high yield.

1 Claim, No Drawings

METHOD OF SEPARATING ERGOSTEROL

RELATED APPLICATIONS

This application is a nationalization of PCT Application No. PCT/JP2003/014170 filed Nov. 7, 2003. This application claims priority from Japanese Patent Application No. 2002-325381 filed on Nov. 8, 2002.

TECHNICAL FIELD

The present invention relates to a method of separating ergosterol.

BACKGROUND ART

Ergosterol is a type of sterols, which is contained in microorganisms such as fungi. It is a substance useful as a provitamin D2. It has been known that when such an ergosterol is crystallized in a water-insoluble organic solvent, granular aggregates exhibiting good solid-liquid separation character can be obtained (Japanese Patent Laid-Open No. 2002-80492). In this case, however, the actual yield of crystals is significantly lower than that estimated from the solubility of ergosterol in the above organic solvent. Thus, this method is problematic in that the remainder of ergosterol are gradually precipitated as fine crystalline flocculates from the filtrate after solid-liquid separation. It has also been known that ergosterol forms hydrate crystals (S. E. Hull et al., Acta Cryst. B32, 2370-2373 (1976)). However, the association of this fact with the aforementioned problem has not been clarified.

SUMMARY OF THE INVENTION

The present invention solves the aforementioned problem regarding poor yield, and provides an industrially advantageous method of separating ergosterol by obtaining ergosterol crystals at a high yield, and preferably by obtaining ergosterol aggregates with good solid-liquid separation character at a high yield.

As a result of various experiments and studies regarding crystallization of ergosterol, the present inventor has found for the first time that water supply during the crystallization of ergosterol largely affects the yield of crystals. He has completed the present invention based on these findings.

The method of separating ergosterol according to the present invention is characterized in that water is supplied to a solution thereof in a water-insoluble organic solvent. According to the present invention, generation of ergosterol crystals is promoted, thereby achieving a higher yield. In addition, by controlling the water supply, generation of ergosterol aggregates with good solid-liquid separation character is promoted, thereby achieving high yield. Moreover, such ergosterol aggregates obtained by controlling water supply contains an amorphous component in a crystal thereof, and has a crystallinity of approximately 50% to 90%.

That is to say, the present invention relates to a method of separating ergosterol from a solution containing ergosterol in water-insoluble organic solvent, which comprises supplying water to said solution and precipitating ergosterol.

Moreover, the present invention relates to the above described method, wherein an amount of the water supplied is within such a range of amount that no phase separation to form two liquid phases occurs between the water-insoluble organic solvent and water.

Furthermore, the present invention relates to: the above described method, wherein the solution containing ergosterol in the water-insoluble organic solvent is a solution extracted from a microorganism containing the ergosterol using the water-insoluble organic solvent, or a solution obtained by extracting ergosterol from the microorganism using another solvent and then replacing said another solvent with the water-insoluble organic solvent;

the above described method, wherein the water-insoluble organic solvent is hexane, heptane, octane, or a mixture thereof;

the above described method, wherein supplying water is conducted by continuously or intermittently moisturizing a gas phase portion within an apparatus for precipitating ergosterol; and the above described method, wherein ergosterol is separated by precipitation as an aggregate having a crystallinity of 50% to 90%.

Still further, the present invention relates to an ergosterol aggregate having a crystallinity of 50% to 90%.

DETAILED DESCRIPTION OF THE INVENTION

The present invention will be described in detail below.

The method of separating ergosterol of the present invention is characterized in that it comprises supplying water to a solution thereof in a water-insoluble organic solvent containing ergosterol, so as to precipitate ergosterol.

Ergosterol is a type of sterols, which is contained in microorganisms such as fungi. It is a substance useful as a provitamin D2. Representative fungi containing ergosterol may include: mushrooms such as *Lentinus edodes* or *Grifola frondosa*; yeasts; and leguminous bacteria found in roots of leguminous plants. In addition, other microorganisms containing ergosterol may include unicellular algae such as Chlorella.

The term "water-insoluble organic solvent" is used in the present invention to mean a substance that is generally considered to be insoluble or hardly soluble in water based on Material Safety Data Sheets, for example. Specific examples of such a water-insoluble organic solvent may include: aliphatic hydrocarbons such as hexane, heptane, or octane; aromatic hydrocarbons such as benzene, toluene, or xylene; and halogenated hydrocarbons such as methylene chloride, chloroform, or carbon tetrachloride. These solvents may be used singly or in combination of two or more types. In terms of necessity of conducting an ergosterol precipitation operation, among the aforementioned solvents, aliphatic hydrocarbons are preferable because the solubility of ergosterol is low therein. Of these, hexane, heptane, octane, and a mixture thereof are more preferable.

Examples of a solution containing ergosterol in a water-insoluble organic solvent may include: a solution thereof in a water-insoluble organic solvent in which only ergosterol is dissolved; a solution extracted from a microorganism containing the ergosterol, such as fungi, using a water-insoluble organic solvent; and a solution obtaining by extracting ergosterol from a microorganism containing ergosterol, such as fungi, by using another solvent and then replacing said another solvent with the water-insoluble organic solvent.

Examples of another solvent used for extraction may include: water-soluble organic solvent such as acetone, ethanol, or 2-propanol; and mixtures comprising these water-soluble organic solvents and the aforementioned water-insoluble organic solvents.

When ergosterol is extracted from a microorganism containing the ergosterol, such as fungi, using a water-insoluble organic solvent, the obtained extract may directly be used in the subsequent precipitation step. Otherwise, after ergosterol has been extracted with a water-insoluble organic solvent (aromatic hydrocarbon or halogenated hydrocarbon) in which the solubility of ergosterol is high, the water-insoluble organic solvent may be exchanged with another water-insoluble organic solvent (aliphatic hydrocarbon) in which the solubility of ergosterol is low. The thus obtained solution may be used in the subsequent precipitation step.

When ergosterol is precipitated from a solution thereof in a water-insoluble organic solvent containing the ergosterol, generally known methods can be applied. Examples of such known methods may include: cooling crystallization of decreasing the temperature of a solution to decrease solubility, so as to precipitate a product of interest; and evaporation crystallization of evaporating an organic solvent for concentration, so as to precipitate a product of interest. In the present invention, the cooling crystallization is applied more preferably than the evaporation crystallization in which water is evaporated and lost by azeotropy or the like.

A system for precipitating ergosterol is not particularly limited. Examples of such a system may include: a batch crystallizer using an agitation tank equipped with a jacket; a continuous crystallizer for continuously supplying and discharging the liquid from one or more agitation tanks equipped with a jacket; and a continuous tower crystallizer.

In the present invention, water is supplied to precipitate ergosterol. An amount of the water supplied is within such a range of amount that no phase separation to form two liquid phases occurs between the water-insoluble organic solvent. The term "such a range of amount that no phase separation to form two liquid phases occurs between the water-insoluble organic solvent" is used herein to mean a trace amount of water that can be dissolved in a water-insoluble organic solvent. Such an amount of water is associated with water solubility in the water-insoluble organic solvent, and thus, it varies somewhat depending on the type of a water-insoluble organic solvent. When hexane is used as such a water-insoluble organic solvent, for example, the amount of water is preferably approximately 1 to 100 ppm with respect to the hexane.

If the amount of water is too large, the water-insoluble organic solvent solution is separated into two liquid phases, a water-insoluble organic solvent phase and water phase. As a result, it becomes difficult to handle, and also ergosterol appears as needle crystals, thereby resulting in a rather poorer solid-liquid separation character. In contrast, if no water is supplied, crystals are not precipitated, and the yield thereby decreases.

If water is supplied in a liquid form, even within a range where the solution is not separated into two liquid phases, the liquid phase transiently may become nonuniform, and needle crystals may then be formed at a position where water is localized. In order to prevent such a phenomenon, it is preferable that water is supplied by moisturizing a gas phase portion (a portion where the gas exists) in a system for precipitating ergosterol, so as to maintain the liquid phase in a uniform state.

A method of moisturizing a gas phase portion is not particularly limited, as long as it can supply water to such an extent that the water-insoluble organic solvent solution is not separated into two liquid phases. Examples of such a method may include: direct feeding of steam; flowing of nitrogen gas or the like that has passed through water; supply of misty water generated using an ultrasonic humidifier; and flowing of a gas that has passed though the misty water as generated above.

Moreover, it is preferable that water is supplied continuously or intermittently. More preferably, water is supplied by continuously or intermittently moisturizing a gas phase portion of a system for precipitating ergosterol.

A crystallization temperature is preferably −30° C. to 80° C., and more preferably −20° C. to 60° C. A crystallization time is preferably 0.5 to 24 hours, and more preferably 1 to 6 hours. When crystallization is carried out by gradual cooling, a cooling rate is preferably 0.05° C. to 3° C./min, and more preferably 0.1° C. to 1° C./min.

After ergosterol has been precipitated as described above, solid-liquid separation is conducted by filtration or the like, so as to separate ergosterol. Thereafter, the separated ergosterol is dried at ordinary temperature or while warming, under ordinary or reduced pressure, so as to obtain ergosterol crystals.

The recovery rate of ergosterol is preferably 60% or more, more preferably 70% or more, further preferably 80% or more, and particularly preferably 90% or more.

Ergosterol precipitated and separated by particularly controlling the water supply in the method of separating ergosterol of the present invention is a granular ergosterol aggregate with good solid-liquid separation character. This aggregate does not only comprise generally known hydrate crystals, but also comprises amorphous component as well as hydrate crystals in the crystals thereof. Since such amorphous component contain no crystal water, an aggregate can efficiently be precipitated with water supply that are smaller than those necessary for obtaining the aggregate entirely in the form of hydrate crystals, thereby improving the yield. Thus, it is preferable that the amount of such amorphous component is larger. However, if the amount is too large, the resultant product cannot be obtained in the form of an aggregate. Accordingly, the crystallinity of an ergosterol aggregate is preferably 50% to 90%, and more preferably 60% to 80%.

Since an aggregate with such characteristics still requires a minute amount of water to constitute crystal component, if no water is supplied during the precipitation of ergosterol, water contained in the system will be consumed up, so that the yield cannot be increased.

The aforementioned crystallinity can be measured by X-ray diffraction or the like. Moreover, it can also be obtained by measuring water of hydration by thermogravimetric analysis. Herein, the value obtained by measuring by thermogravimetric analysis is adopted as a crystallinity. That is, an aggregate that has been dried by air so as not to lose crystal water is subjected to thermogravimetric analysis, so that the water content thereof is measured, thereby obtaining the amount of crystal component in the aggregate, that is, a crystallinity.

Specifically, such a crystallinity can be obtained as follows. It is considered that the crystal component in the air-dried aggregate correspond to a monohydrate and that the amorphous component contains no water. Thus, the number of moles of water present in the aggregate=the number of moles of crystals. In addition, when the weight of a sample subjected to the analysis is expressed as W and the loss weight measurement is expressed as $\Delta w$, the following formulas hold:

The number of moles of crystals $(Mc) = \Delta w/$the molecular weight of water; and The total number of moles of ergosterol $(M) = (W − \Delta w)/$the molecular weight of ergosterol. Thus, a crystallinity is obtained by the following formula:

$$\text{Crystallinity} = (Mc/M) \times 100.$$

The particle size of the obtained granular aggregate is preferably 50 μm or greater, and more preferably 100 μm or greater.

BEST MODE FOR CARRYING OUT THE INVENTION

The present invention will be further described in the following examples. However, the examples are not intended to limit the scope of the present invention.

EXAMPLE 1

500 ml of a hexane solution containing ergosterol with a concentration of 4 g/L was filtrated and then placed in a batch crystallizer equipped with a 500 ml separable flask. While stirring, the solution was cooled at a cooling rate of 0.2° C./min until the liquid temperature decreased from 45° C. to 10° C. After the liquid temperature became 35° C., the upper portion of the flask was opened every 25 minutes, so that using a syringe, 100 ml each of the air moisturized with hot water at 40° C. was fed into the flask. After completion of the cooling crystallization the solid was separated from the liquid using a vacuum filtration system, and then the solid was dried, so as to obtain an aggregate. The thus obtained crystal was a granular aggregate having a particle size between 100 μm and 200 μm. The granular aggregate exhibited good solid-liquid separation character, and the recovery rate (obtained by measuring the concentration of the solution using the additive amount as a standard) was also favorable, resulting in 78%. In addition, the reduced weight was measured by increasing the temperature from 30° C. to 180° C. at a rate of 10° C./min, using a thermogravimetric system (TG/DTA220; manufactured by Seiko Instruments Inc.), so as to obtain a crystallinity. As a result, the crystallinity of this aggregate was found to be 66%.

EXAMPLE 2

A hexane solution containing ergosterol whose concentration had been adjusted to be 4 g/L was continuously supplied to a continuous tower crystallizer having an inside diameter of 30 mm and a height of 450 mm. The crystallizer was operated under conditions consisting of: the temperature of a discharging port at the head of the tower of 10° C.; a rotation rate by stirring of 100 rpm; a liquid-supplying rate of 5 ml/min (wherein the supplied liquid was maintained at approximately 50° C.); and a mean retention time of 60 minutes. A nitrogen gas, which was moisturized by passing it through a trap tube containing water, was flown through a gas phase portion from a nozzle located at the top end of the above system. Crystals precipitated and sedimented in the system were sampled. As a result, it was found that the crystal was a granular aggregate with a particle size of approximately 200 μm, which exhibited good solid-liquid separation character. After completion of the operation for 1 hour, the recovery rate (obtained by measuring the concentration of the solution existing the exit of the system, using the additive amount as a standard) was favorable, resulting in 77%. Moreover, thermogravimetric analysis was carried out in the same above manner. As a result, this crystal was found to have a crystallinity of 60%.

EXAMPLE 3

Hexane solution (500 ml) containing ergosterol with a concentration of 4 g/L was filtrated and then added to a batch crystallizer of a 500 ml separable flask. While stirring, the solution was cooled at a cooling rate of 0.2° C./min until the liquid temperature decreased from 45° C. to 10° C. During the cooling, 0.5 ml of water was added. The added water could not be dissolved in hexane, and existed as a droplet until completion of the cooling. After completion of the cooling, the solid was separated from the liquid, and a crystal was collected after drying it under reduced pressure. The recovery rate (obtained by measuring the concentration of the solution using the additive amount as a standard) was favorable, resulting in 87%. However, the crystal had a needle form. Moreover, thermogravimetric analysis was carried out in the same above manner. As a result, this crystal was found to have a crystallinity of 95%.

COMPARATIVE EXAMPLE 1

A hexane solution (500 ml) containing ergosterol with a concentration of 4 g/L was filtrated and then added to a batch crystallizer of a 500 ml separable flask. While stirring, the solution was cooled at a cooling rate of 0.2° C./min until the liquid temperature decreased from 45° C. to 10° C. The system was hermetically sealed until the cooling operation was completed. After completion of the cooling, the solid was separated from the liquid, and a crystal was collected after drying it under reduced pressure. The obtained crystal was a granular aggregate having a particle size of approximately 200 μm, which exhibited good solid-liquid separation character. However, the recovery rate (obtained by measuring the concentration of the solution using the additive amount as a standard) was poor, resulting in 53%.

INDUSTRIAL APPLICABILITY

The present invention makes it possible to obtain ergosterol crystals at a high yield. Moreover, by controlling the water supply, it becomes possible to obtain a granular ergosterol aggregate exhibiting good solid-liquid separation character at a high yield.

The invention claimed is:
1. A method of separating ergosterol from a solution containing ergosterol in hexane, which comprises:
supplying a trace amount of water to said solution and precipitating ergosterol from said solution containing ergosterol in hexane by cooling crystallization,
wherein the trace amount of water supplied is between 1 and 100 ppm with respect to the hexane, and no phase separation to form two liquid phases occurs between the hexane and water.

* * * * *